United States Patent [19]

Richarz et al.

[11] Patent Number: 4,820,704
[45] Date of Patent: Apr. 11, 1989

[54] PYRIDAZINONE DERIVATIVES AND THEIR USE AS FUNGICIDES

[75] Inventors: Winfried Richarz; Gernot Reissenweber, both or Ludwigshafen; Ernst-Heinrich Pommer, Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 754,666

[22] Filed: Jul. 11, 1985

Related U.S. Application Data

[63] Continuation of Ser. No. 435,963, Oct. 22, 1982, abandoned.

[51] Int. Cl.$^4$ ............... C07D 237/14; A01N 43/58
[52] U.S. Cl. ................... 514/247; 514/252; 544/239; 544/240
[58] Field of Search ............... 544/240, 239; 514/247, 514/252

[56] References Cited

U.S. PATENT DOCUMENTS

| | | | |
|---|---|---|---|
| 3,050,440 | 8/1962 | Richter et al. | 514/708 |
| 3,063,824 | 11/1962 | Curtis et al. | 514/709 X |
| 3,137,696 | 6/1964 | Reicheneder et al. | 544/252 |
| 3,186,904 | 7/1965 | Stevenson et al. | 514/708 |
| 4,089,964 | 5/1978 | Sugiyama et al. | 514/708 |

FOREIGN PATENT DOCUMENTS 1445475  2/1962  Fed. Rep. of Germany.

OTHER PUBLICATIONS

The Agrochemicals Handbook, 2nd Ed., Royal Society of Chemistry, Nottingham, England, Aug. 1987.
Chemical Abstracts, vol. 90, 1979, 87377h.
Chemical Abstracts, vol. 70, 1969, 68398m.
Chemical Abstracts, vol. 70, 1969, 68397k.
Chemical Abstracts, vol. 88, 1978, 37821m.
Chemical Abstracts, vol. 87, 1977, 201567k.
Chemical Abstracts, vol. 75, 1971, 129060x.
Chemical Abstracts, vol. 72, 1970, 55374s.
Takahashi et al, Yakugaku Zasshi, vol. 89 (1969), pp. 1516–1527.

*Primary Examiner*—David B. Springer
*Attorney, Agent, or Firm*—Keil & Weinkauf

[57] ABSTRACT

Pyridazinone derivatives of the formula

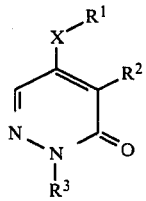

(I)

where $R^1$ is alkyl, alkenyl, cycloalkyl or unsubstituted or substituted phenyl, $R^2$ is chlorine or bromine, $R^3$ is hydrogen, alkyl, cycloalkyl or unsubstituted or substituted phenyl and X is SO or $SO_2$, with the proviso that $R^1$ is not methyl when X is $SO_2$, $R^2$ is chlorine and $R^3$ is phenyl, and fungicides containing these compounds.

6 Claims, No Drawings

PYRIDAZINONE DERIVATIVES AND THEIR USE AS FUNGICIDES

This application is a continuation of application Ser. No. 435,963, filed on Oct. 22, 1982, abandoned.

The present invention relates to novel pyridazinone derivatives which are substituted in the 4-position by a sulfinyl or sulfonyl group, a process for their preparation, fungicides containing these compounds as active ingredients, and a process for controlling fungi with these fungicides.

German Laid-Open Application DOS No. 1,445,475 discloses that pyridazinone derivatives of the formula

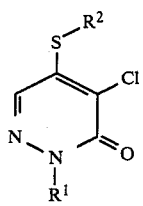

where $R^1$ is an unsubstituted or substituted alkyl, cycloalkyl or aryl radical and $R^2$ is hydrogen or an unsubstituted or substituted alkyl, alkenyl, cycloalkyl, acyl or aralkyl radical, can be used as agents for influencing plant growth.

Furthermore, Yakugaku Zasshi 89 (1969), 1516–1527 discloses that 1-phenyl-4-methylsulfonyl-5-chloropyridazin-6-one has bactericidal and fungicidal actions.

We have found that pyridazinone derivatives of the general formula I

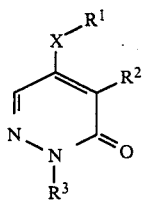

where $R^1$ is alkyl, alkenyl, cycloalkyl or unsubstituted or substituted phenyl, $R^2$ is chlorine or bromine, $R^3$ is hydrogen, alkyl, cycloalkyl or unsubstituted or substituted phenyl and X is SO or $SO_2$, with the proviso that $R^1$ is not methyl when X is $SO_2$, $R^2$ is chlorine and $R^3$ is phenyl, have an excellent fungicidal action.

$R^1$ is, for example, methyl, ethyl, propyl, i-propyl, tert.-butyl, cyclohexyl, phenyl or p-chlorophenyl, and $R^3$ is, for example, hydrogen, methyl, ethyl, i-propyl, cyclohexyl, phenyl, 4-chlorophenyl, 3,5-dichlorophenyl, 4-bromophenyl, 3-trifluoromethylphenyl, 3-methylphenyl, 4-methylphenyl, 4-acetoxyphenyl or 3-(pentafluoroethoxy)-phenyl.

The pyridazinone derivatives of the formula I can be obtained by oxidizing a pyridazinone of the formula II

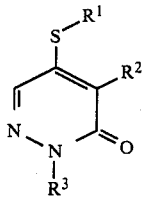

where $R^1$, $R^2$ and $R^3$ have the above meanings, with hydrogen peroxide or a per-acid, in the presence or absence of a solvent or diluent, at from 0° to 100° C. Examples of solvents or diluents which may be used are glacial acetic acid and acetone. For examples, to prepare the pyridazinones of the formula I where X is SO, it is advantageous to use about 1.0–1.1 moles of oxidizing agent (hydrogen peroxide or a per-acid) per mole of a pyridazinone of the formula II, and to prepare the pyridazinones of the formula I where X is $SO_2$, it is advantageous to use from 2.0 to 5.0 moles of oxidizing agent per mole of a pyridazinone of the formula II. The reaction is carried out in general at from 0° to 100° C., for example for from 1 to 100 hours, under atmospheric or superatmospheric pressure, either continuously or batchwise.

In a preferred embodiment of the novel process, hydrogen peroxide is added to a solution of the starting material of the formula II in glacial acetic acid, and the reaction mixture is kept at from 0° to 100° C., preferably from 60° to 80° C., for from 1 to 100 hours, preferably from 4 to 20 hours.

To isolate the pyridazinones of the formula I, for example, the reaction mixture is cooled to 0° C. and the precipitated crystals are filtered off under suction. The mother liquor may be reused for a further reaction. Another possible method of isolating the novel substances comprises diluting the reaction mixture with water and filtering off under suction the precipitate which separates out as a result. The products after washing with water generally do not require further purification but may, if required, be purified further by a conventional method, for example by recrystallization, extraction or chromatography.

The pyridazinones of the formula II which are used for the preparation of the pyridazinones of the formula I can be obtained by reacting a pyridazinone of the formula III

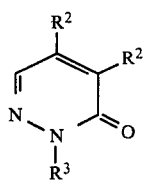

where $R^2$ and $R^3$ have the above meanings, with a thiol of the formula III

$R^1$—SH         IV where $R^1$ has the above meanings, in the presence or absence of a solvent or diluent, in the presence of an inorganic or organic base and in the presence or absence of a reaction accelerator, at from −20° to +120° C.

Preferred solvents or diluents, where the reaction is carried out in the presence of these, are halohydrocarbons, eg. methylene chloride, chloroform, 1,2-dichloroethane or chlorobenzene, aliphatic or aromatic hydrocarbons, eg. cyclohexane, petroleum ether, benzene, toluene or xylenes, esters, eg. ethylacetate, nitriles, eg. acetonitrile, sulfoxides, eg. dimethylsulfoxide, ketones, eg. acetone or methyl ethyl ketone, ethers, eg. diethyl ether, tetrahydrofuran and dioxane, and mixtures of these.

Advantageously, the solvent or diluent is used in an amount of from 100 to 2,000, preferably from 100 to 1,000, % by weight, based on the starting material of the formula II or III.

Examples of suitable inorganic or organic bases which may be added, as acid acceptors, to the reaction mixture are alkali metal carbonates, eg. potassium carbonate or sodium carbonate, alkali metal hydrides, eg. sodium hydride, tertiary amines, eg. trimethylamine, triethylamine, N,N-dimethylaniline, N,N-dimethylcyclohexylamine, N-methylpiperidine or pyridine, and azoles, eg. 1,2,4-triazole or imidazole, but other conventional bases may also be used. Preferred reaction accelerators are metal halides, eg. sodium bromide and potassium iodide, azoles, eg. imidazole, pyridines, eg. 4-methylpyridine, and quaternary ammonium salts, eg. N,N-dibenzyl-N,N-dimethylammonium chloride, as well as mixtures of these.

Advantageously, from 1.0 to 2.0 moles of a thiol of the formula IV and, where relevant, from 0.5 to 2 moles of a base and, where relevant, from 0.01 to 0.1 mole of a reaction accelerator are employed per mole of a pyridazinone of the formula III.

The reaction is carried out in general at from $-20°$ to $+120°$ C., for example for from 1 to 80 hours, under atmospheric or superatmospheric pressure, either continuously or batchwise.

In a preferred embodiment of the novel process, a solution of the starting material of the formula III in one of the above solvents or diluents is mixed with dilute aqueous alkali and if appropriate the reaction accelerator in the form of a quaternary ammonium salt, the thiol derivative is added and the reaction mixture is kept at from $-20°$ to $+120°$ C. for from 0.5 to 12, preferably from 1 to 6, hours.

To isolate the thiolpyridazinone of the formula II, the organic phase is separated off, and washed with water. The product which remains after the solvent has been distilled off can, if required, be purified further by a conventional method, for example by recrystallization, extraction or chromatography.

Some of the pyridazinone derivatives of the general formula III which are employed as starting materials are known; both these and the unknown pyridazinone derivatives can be prepared using a conventional process, by reacting mucochloric acid or mucobromic acid with a hydrazine of the formula V $$H_2-NH-R^3 \quad\quad V$$

where $R^3$ has the above meanings.

The method below illustrates the preparation of the pyridazinone derivatives of the formula II which are required in order to prepare the novel active ingredients of the formula I. Parts by weight bear the same relation to parts by volume as that of the kilogram to the liter.

METHOD 38.3 parts by weight of cyclohexylthiol were added dropwise to a mixture of 72.3 parts by weight of 1-phenyl-4,5-dichloropyridazin-6-one in 300 parts by volume of methylene chloride, 3 parts by weight of triethylbenzylammonium chloride, and 13.2 parts by weight of sodium hydroxide in 150 parts by volume of water at room temperature (20° C.), and the reaction mixture was kept at this temperature for 12 hours, while stirring vigorously. The organic phase was separated off, washed with twice 100 parts by volume of water, dried and then concentrated. The residue was recrystallized from ethylacetate. 61 parts by weight of 1-phenyl-4-(cyclohexylthio)-5-chloropyridazin-6-one of melting point 125°–127° C. were obtained (compound A1).

$C_{16}H_{17}ClN_2SO$ (320.5).

Calculated: C 59.9, H 5.34, N 8.73, S 9.99.

Found: C 60.0, H 5.5, N 8.7, S 10.1.

The following compounds of the formula II can be prepared by methods corresponding to that above.

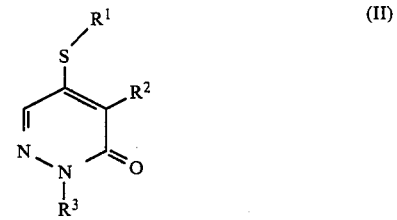

| No. | R¹ | R² | R³ | Mp. (°C.) |
|---|---|---|---|---|
| A2 | CH₃ | Cl | C₆H₅ | 116–117 |
| A3 | C₂H₅ | Cl | C₆H₅ | 92–93 |
| A4 | C₂H₅ | Cl | 4-chlorophenyl | 140–142 |
| A5 | C₂H₅ | Cl | 4-bromophenyl | 135–136 |
| A6 | C₂H₅ | Cl | 3,5-dichlorophenyl | 157–158 |
| A7 | C₂H₅ | Cl | 4-acetoxyphenyl | 164–165 |
| A8 | C₂H₅ | Cl | 3-acetarylphenyl | 89–90 |
| A9 | C₂H₅ | Cl | 3-trifluoromethylphenyl | 137–138 |
| A10 | C₂H₅ | Cl | 4-(3'-trifluoromethylphenoxy)-phenyl | 93–95 |
| A11 | i-propyl | Cl | phenyl | 115–117 |
| A12 | tert.-butyl | Cl | phenyl | 78–79 |
| A13 | phenyl | Cl | phenyl | 110–112 |
| A14 | phenyl | Cl | 3,5-dicholophenyl | 87–88 |
| A15 | phenyl | Cl | 3-trifluoromethylphenyl | 96–97 |
| A16 | phenyl | chlorine | methyl | 105–106 |
| A17 | 4-chlorophenyl | chlorine | phenyl | 193–195 |
| A18 | cyclohexyl | chlorine | 3-trifluoromethylphenyl | 112–114 |
| A19 | cyclohexyl | bromine | phenyl | 113–115 |

The examples which follow illustrate the preparation of the novel pyridazinone derivatives of the formula I. Parts by weight bear the same relation to parts by volume as that of the kilogram to the liter.

EXAMPLE 1

5.1 parts by volume of 30% strength by weight hydrogen peroxide were added dropwise to a solution of 16 parts by weight of 1-phenyl-4-(cyclohexylthio)-5-chloropyridazin-6-one in 100 parts by volume of glacial acetic acid, and stirring was continued for 12 hours at 60° C. The reaction mixture was then stirred into 1,000 parts by volume of water, and the precipitate was filtered off under suction, washed with water and dried under reduced pressure. 16.3 parts by weight of 1-phenyl-4-(cyclohexyl-sulfinyl)-5-chloropyridazin-6-one of melting point 128°–130° C. were obtained (compound No.1).

$C_{16}H_{17}ClN_2O_2S$ (336.5).
Calculated: C 57.1, H 5.1, N 8.3, Cl 10.5, S 9.5.
Found: C 57.2, H 5.1, N 8.2, Cl 10.2, S 9.6.

EXAMPLE 2

25 ml of 30% strength hydrogen peroxide were added dropwise to a solution of 16 parts by weight of 1-phenyl-4-(cyclohexylthio)-5-chloropyridazin-6-one in 100 parts by volume of glacial acetic acid at room temperature, and stirring was continued for 5 hours at 50° C. After the reaction mixture had cooled, the product was filtered off under suction, washed with water and dried under reduced pressure. 13.8 parts by weight of 1-phenyl-4-(cyclohexylsulfonyl)-5-chloropyridazin-6-one of melting point 195°–196° C. were obtained (compound No.2).

$C_{16}H_{17}ClN_2SO_3$ (352.5).
Calculated: C 54.5 H 4.9 N 7.9 Cl 10.0 S 9.1.
Found: C 54.6 H 4.8 N 7.9 Cl 9.9 S 9.0.

The compounds of the formula I which are listed in the table below were prepared in a similar manner, their melting points being given in the table. Their structures were established by elementary analysis. The compounds for which no physicochemical data are given can be obtained in the same manner as the compounds which were actually prepared. It is to be expected that, because they have structures similar to those of the compounds investigated in more detail, they will also have similar actions.

| No. | R¹ | R² | R³ | X | M.p. (°C.) |
|---|---|---|---|---|---|
| 3 | ethyl | chloro | phenyl | SO | 142–143 |
| 4 | ethyl | chloro | phenyl | SO₂ | 178–180 |
| 5 | ethyl | chloro | 4-chlorophenyl | SO | 127–129 |
| 6 | ethyl | chloro | 4-chlorophenyl | SO₂ | 181–183 |
| 7 | ethyl | chloro | 4-acetoxyphenyl | SO | 149–151 |
| 8 | ethyl | chloro | 4-acetoxyphenyl | SO₂ | 197–199 |
| 9 | cyclohexyl | chloro | 3-trifluoromethylphenyl | SO | 169–170 |
| 10 | cyclohexyl | chloro | 3-trifluoromethylphenyl | SO₂ | 158–160 |
| 11 | ethyl | chloro | 3-methylphenyl | SO | oil |
| 12 | ethyl | chloro | 4-bromophenyl | SO₂ | 149–151 |
| 13 | ethyl | chloro | 4-bromophenyl | SO | 157–158 |
| 14 | ethyl | chloro | 4-bromophenyl | SO₂ | 165–166 |
| 15 | phenyl | chloro | 3,5-dichlorophenyl | SO | 157–158 |
| 16 | phenyl | chloro | 3,5-dichlorophenyl | SO₂ | 194–196 |
| 17 | ethyl | chloro | 3,5-dichlorophenyl | SO | 99–101 |
| 18 | ethyl | chloro | 3,5-dichlorophenyl | SO₂ | 142–143 |
| 19 | phenyl | chloro | 3-trifluoromethylphenyl | SO | 140-141 |
| 20 | phenyl | chloro | 3-trifluoromethylphenyl | SO₂ | 136–138 |
| 21 | ethyl | chloro | 3-trifluoromethylphenyl | SO | 120–121 |
| 22 | ethyl | chloro | 3-trifluoromethylphenyl | SO₂ | 139–140 |
| 23 | phenyl | chloro | phenyl | SO | 122–123 |
| 24 | p-chlorophenyl | chloro | phenyl | SO | 164–165 |
| 25 | tert.-butyl | chloro | phenyl | SO₂ | 192–193 |
| 26 | i-propyl | chloro | phenyl | SO₂ | 150–151 |
| 27 | ethyl | chloro | 4-(3'-trifluoromethylphenoxy)-phenyl | SO | 74–75 |
| 28 | ethyl | chloro | 4-(3'-trifluoromethyl-phenoxy)-phenyl | SO₂ | 138–139 |
| 29 | ethyl | chloro | isopropyl | SO | oil |
| 30 | ethyl | chloro | isopropyl | SO₂ | 135–136 |
| 31 | cyclohexyl | chloro | isopropyl | SO | |
| 32 | cyclohexyl | chloro | isopropyl | SO₂ | |
| 33 | ethyl | chloro | methyl | SO | 83 |
| 34 | ethyl | chloro | methyl | SO₂ | 138–139 |
| 35 | ethyl | chloro | cyclohexyl | SO | |
| 36 | ethyl | chloro | cyclohexyl | SO₂ | |
| 37 | cyclohexyl | chloro | cyclohexyl | SO | |
| 38 | cyclohexyl | chloro | cyclohexyl | SO₂ | |
| 39 | allyl | chloro | phenyl | SO | |
| 40 | allyl | chloro | phenyl | SO₂ | |
| 41 | methyl | chloro | 3,5-dichlorophenyl | SO | |
| 42 | methyl | chloro | 3,5-dichlorophenyl | SO₂ | |
| 43 | cyclohexyl | bromo | phenyl | SO | |
| 44 | cyclohexyl | bromo | phenyl | SO₂ | |

The novel active ingredients have a strong action on phytopathogenic fungi, and are particularly suitable for preventing or curing plant diseases, e.g., *Botrytis cinerea* in vines, strawberries and pimientos, *Monilia fructigena* in apples and pears, *Plasmopara viticola* in vines, *Pseudoperonospora* in hops, *Peronospora halstedii* in sunflowers, *Peronospora tabacina* in tobacco, *Septoria nodorum* in cereals, *Septoria glycinea* in soybeans, *Phytophthora infestans* in potatoes and tomatoes, *Cercospora beticola* in beets, *Pseudocercosporella herpotrichoides* in wheat and barley, *Pyricularia oryzae* in rice, and *Pseudoperonospora cubensis* in cucumbers.

The novel compounds are applied by spraying or dusting the plants, or treating the seed with the active ingredients. Application may be effected before or after infection of the plants or seed by the fungi.

The compounds according to the invention may be converted into the usual formulations, e.g. solutions, emulsions, suspensions, dusts, powders, pastes and granules. The forms of application depend entirely on the purpose for which the agents are being used, but they must ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt% of active ingredient.

The application rates depend on the effect desired, and range from 0.1 to 3 kg of active ingredient per hectare, or more. The novel compounds may also be used to protect materials, e.g., as fungicides for surface coatings and soft PVC; the application rates are from 0.05 to 5% (by weight) of active ingredient, based on the total weight of the paints to be preserved or the PVC to be microbicidally treated.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of the compound of Example 5 is mixed with 10 parts by weight of N-methyl-alpha-pyrrolidone. A mixture is obtained which is suitable for application in the form of very fine drops.

II. 10 parts by weight of the compound of Example 6 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 12 is dissolved in a mixture consisting of 60 parts by weight of cyclohexanone, 30 parts by weight of isobutanol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound no. 5 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 17 is well mixed with 3 parts by weight of the sodium salt of the diisobutylnaphthalenealpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 22 is intimately mixed with 97 parts by weight of particulate kaolin. A dust is obtained containing 3% by weight of the active ingredient.

VII. 30 parts by weight of compound no. 18 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 25 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 26 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may also be mixed and applied with other active ingredients, e.g., herbicides, insecticides, growth regulators, bactericides, fungicides and fertilizers. When mixed with other fungicides, the spectrum of fungicidal action is in many cases increased.

The following list of fungicidal active ingredients with which the compounds according to the invention may be combined is intended to illustrate and not to restrict the combination possibilities.

Examples of fungicides which may be combined with the compounds according to the invention are: sulfur, dithiocarbamates and their derivatives, e.g. iron(III) dimethyldithiocarbamate, zinc dimethyldithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N-polyethylene-bis-(thiocarbamoyl)disulfide, zinc N,N-propylene-bis-dithiocarbamate, and the ammonia complex of zinc N,N-propylene-bis-dithiocarbamate and N,N-polypropylene-bis-(thiocarbamoyl)-disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-(1,1,2,2-tetrachloroethylthio)-tetrahydrophthalimide, N-trichloromethylthiotetrahydrophthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenylsulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, DL-methyl-N-(2,6-dimethylphenyl)-N-fur-2-oyl-alanate, methyl DL-N-(2,6-dimethylphenyl)-N-(2'-methoxyacetyl)-alanate, diisopropyl 5-nitroisophthalate, 1-(1',2',4'-triazol-1'-yl)-[4'-chlorophenoxy]-3,3-dimethylbutan-2-one, 1-(1',2',4'-triazol-1'-yl)-[1-(4'-chlorophenoxy)]-3,3-dimethylbutan-2-ol, N-(2,6-dimethylphenyl)-N-chloroacetyl-D,L-2-aminobutyrolactone, N-(n-propyl)-N-(2,4,6-trichlorophenoxyethyl)-N'-imidazolylurea, N-cyclohexyl-N-methoxy-2,5-dimethylfuran-3-carboxamide, 2,4,5-trimethyfuran-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, N-[3-(p-tert-butylphenyl)-2-methylpropyl]-cis-2,6-dimethylmorpholine, 1-(2,4-dichlorophenyl)-4,4-dimethyl-2-(1,2,4-triazol-1-yl)-pentan-3-ol, α-(2-chlorophenyl)-α-(4-fluorophenyl)-5-pyrimidinemethanol, α-(2-chlorophenyl)-α-(4-chlorophenyl)-5-pyrimidine-methanol, β-([1,1'-biphenyl]-4-yl-oxy)-α-(1,1-dimethylethyl)-1H-1,2,4-triazole-1-ethanol, 1-[2-(2,4-dichlorophenyl)-4-ethyl-1,3-dioxolan-2-yl-methyl]-1H-1,2,4-triazole, 1-[2-(2,4-dichlorophenyl)-4-propyl-1,3-dioxolan-2-yl-methyl]-1H-1,2,4-triazole, 1-[N-propyl-N-[2-(2,4,6-trichlorophenoxy)-ethyl]-carbamoyl]-imidazole, 2-cyano-N-(ethylaminocarbonyl)-2-(methoxyimino)-acetamide, and N-(1-formylamido-2,2,2-trichloroethyl)-morpholine.

For the experiments described below, the following prior art compounds were used for comparison purposes:

A = N—trichloromethylthiotetrahydrophthalimide
(Chemical Week, June 21, 1972, p. 46)

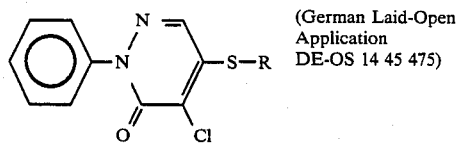
(German Laid-Open Application DE-OS 14 45 475)

B
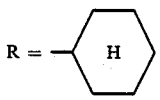

C    R = C$_2$H$_5$
D    R = CH$_3$

E
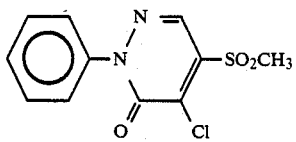

EXPERIMENT 1

Action on *Botrytis cinerea* in pimientos

Pimiento seedlings of the "Neusiedler Ideal Elite" variety were sprayed, after 4 to 5 leaves were well developed, the runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results show that for instance active ingredients 4, 5, 6, 12, 13, 14, 17, 18, 22, 25 and 26, applied as a 0.05% spray, had a better fungicidal action (e.g., 97%) than compounds A, B, C, D, and E (e.g., 70%). When applied as 0.025 or 0.0125% spray liquors, active ingredients 4, 12, 13 and 14 had a better fungicidal action (e.g., 90%) than comparative compounds D and E (e.g., 50%).

EXPERIMENT 2

Action of *Phytophthora infestans* in tomaoes

Leaves of potted tomatoes of the "Grosse Fleischtomate" variety were sprayed with aqueous liquors containing (dry basis) 80% of active ingredient and 20% of emulsifier. After the sprayed-on layer had dried, the leaves were infected witha zoospore suspension of *Phytophthora infestans*. The plants were then placed for 5 days in a steam-saturated chamber kept at 16° to 18° C. After this period, the disease had spread on the untreated control plants to such an extent that the fungicidal action of the compounds was able to be assessed.

The results of this experiment revealed that active ingredients 2, 4, 5, 13, 14, 17, 18, 19, 22, 25 and 26, applied as 0.025% sprays, had a better fungicidal action (e.g., 97%) than active ingredients A, B, C and D (e.g., 50%). When active ingredients 2, 4, 13 and 14 were used as 0.0125% sprays, they had a better fungicidal action (e.g., 97%) than active ingredients D and E (e.g., 70%). When active ingredients 2, 4, 13 and 14 were used as 0.05% sprays, they had an excellent fungicidal action (e.g., 100%).

EXPERIMENT 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspensions of *Plasmopara viticola*. The plants were first placed for 16 hours in a steam-saturated (moist) chamber at 24° C., and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of this experiment revealed that active ingredients 2, 3, 4, 8, 24, 25 and 26, when applied as 0.025% spray liquors, had a good fungicidal action (e.g., 97%).

EXPERIMENT 4

Action on *Septoria nodorum*

Leaves of pot-grown wheat seedlings of the "Jubilar" variety were sprayed with aqueous liquors containing (dry basis) 80% of active ingredient and 20% of emulsifier; after the sprayed-on layer had dried, the leaves were cut off and placed in dishes containing aqueous benzimidazole solution (25 ppm). The leaves were then infected with an aqueous suspension of spores of *Septoria nodorum*, and covered over. The extent of fungus spread was determined after the dishes had stood for 7 days at 20° to 22° C.

The results of this experiment revealed that active ingredients 1, 2, 3, 23 and 24, applied as 0.1% sprays, had a better fungicidal action (e.g., 97%) than active ingredients B and C (e.g., 0%).

We claim:

1. A pyridazinone of the formula

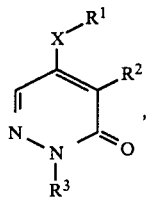

(I)

where $R^1$ is methyl, ethyl, propyl, i-propyl, tert.-butyl, cyclohexyl, phenyl or p-chlorophenyl, $R^2$ is chlorine or bromine, $R^3$ is hydrogen, methyl, ethyl, i-propyl, cyclohexyl, phenyl, 4-chlorophenyl, 3,5-dichlorophenyl, 4-bromophenyl, 3-trifluoromethylphenyl, 3-methylphenyl, 4-methylphenyl, 4-acetoxyphenyl or 3-(pentafluoroethoxy)-phenyl and X is SO or $SO_2$, with the proviso that $R^1$ is not methyl when X is $SO_2$, $R^2$ is chlorine and $R^3$ is phenyl or methyl.

2. A pyridazinone derivative as described in claim 1, where $R^1$ is ethyl or cyclohexyl, $R^2$ is chloro and $R^3$ is phenyl or halophenyl.

3. A process for combating plant pathogenic fungi, wherein the fungi or the agricultural plant or seed threatened by fungus attack are treated with a fungicidally effective amount of a pyridazinone derivative of the formula

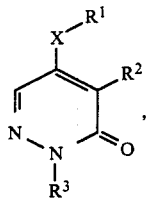

(I)

where $R^1$ is methyl, ethyl, propyl, i-propyl, tert.-butyl, cyclohexyl, phenyl or p-chlorophenyl, $R^2$ is chlorine or bromine, $R^3$ is hydrogen, methyl, ethyl, i-propyl, cyclohexyl, phenyl, 4-chlorophenyl, 3,5-dichlorophenyl, 4-bromophenyl, 3-trifluoromethylphenyl, 3-methylphenyl, 4-methylphenyl, 4-acetoxyphenyl or 3-(pentafluoroethoxy-phenyl and X is SO or $SO_2$, with the proviso that $R^1$ is not methyl when X is $SO_2$, $R^2$ is chlorine and $R^3$ is phenyl.

4. A process as defined in claim 3 wherein $R^1$ of the pyridazinone derivative is ethyl or cyclohexyl, $R^2$ is chloro and $R^3$ is phenyl or halophenyl.

5. A fungicidal formulation for combatting plant pathogenic fungi which comprises: an extender and from 0.5 to 90% by weight of a pyridazinone derivative of the formula I of claim 1.

6. A fungicidal formulation as described in claim 5 wherein $R^1$ of the pyridazinone derivative is ethyl or cyclohexyl, $R^2$ is chloro and $R^3$ is phenyl or halophenyl.

* * * * *

UNITED STATES PATENT AND TRADEMARK OFFICE
CERTIFICATE OF CORRECTION

PATENT NO. : 4,820,704

DATED : April 11, 1989

INVENTOR(S) : RICHARZ et al

It is certified that error appears in the above-identified patent and that said Letters Patent is hereby corrected as shown below:

On the title page Insert

-- (30) Foreign Application Priority Data

Oct. 31, 1981 Fed. Rep. of Germany. . . . 3143303 --.

Signed and Sealed this

Second Day of January, 1990

Attest:

JEFFREY M. SAMUELS

*Attesting Officer*       *Acting Commissioner of Patents and Trademarks*